United States Patent [19]

Pilz et al.

[11] Patent Number: 4,713,201

[45] Date of Patent: Dec. 15, 1987

[54] PROCESS FOR THE PREPARATION OF SALTS OF A DICARBOXYLIC ACID AND A DIAMINE

[75] Inventors: Georg Pilz, Neustadt; Gert Buerger, Mannheim; Manfred Barl, Otterstadt; Gerhard Thiel, Ludwigshafen, all of Fed. Rep. of Germany

[73] Assignee: BASF Aktiengesellschaft, Ludwigshafen, Fed. Rep. of Germany

[21] Appl. No.: 875,547

[22] Filed: Jun. 18, 1986

[30] Foreign Application Priority Data

Jun. 21, 1985 [DE] Fed. Rep. of Germany ....... 3522216

[51] Int. Cl.$^4$ ............................................. C07C 83/00
[52] U.S. Cl. ............................ 260/501.17; 260/501.18
[58] Field of Search ..................... 260/501.17, 501.18

[56] References Cited

U.S. PATENT DOCUMENTS 4,165,335  8/1979  Strehler et al. ................. 260/501.2

Primary Examiner—Paul J. Killos
Attorney, Agent, or Firm—Keil & Weinkauf

[57] ABSTRACT

A process for the preparation of salts of dicarboxylic acids and diamines of the formula $$H_2N\text{-}(R^1\text{-}O)_n\text{-}R^2\text{-}NH_2 \qquad I$$

where $R^1$ and $R^2$ may be identical or different and are each alkylene of 2 to 4 carbon atoms and n is an integer from 1 to 3, which contain hydrazine in the form of hydrazine hydrate.

3 Claims, No Drawings

PROCESS FOR THE PREPARATION OF SALTS OF A DICARBOXYLIC ACID AND A DIAMINE

Salts of dicarboxylic acids and diamines, such as hexamethylenediammonium adipate, are produced in large amounts and used as starting materials for the preparation of nylons by polycondensation. The properties of such nylons have to meet very high requirements. This also applies, therefore, to the salts of dicarboxylic acids and diamines, these salts being used as starting materials, and to the dicarboxylic acids and diamines used for the preparation of such salts. Salts of 4,7-dioxadecane-1,10-diamine, purified by distillation, and dicarboxylic acids have also been prepared. However, salts obtained in this manner do not meet the requirements set. It is in fact known that amines are stabilized to atmospheric oxygen by adding small amounts of hydrazine. Furthermore, U.S. Pat. No. 4,165,335 discloses that hydrazine hydrate is added to alkanediamines in order to improve the quality of the color of the salts prepared from them. Despite the chemically different nature of 4,7-dioxadecane-1,10-diamine, no information was given to indicate the procedure to be adopted in order to achieve all the required characteristics. This is all the more important since the disadvantageous properties are due to very small amounts of impurities whose nature in unknown to date and which to date cannot be removed at an acceptable cost by the conventional purification methods.

It is an object of the present invention to provide salts of dicarboxylic acids and diamines which contain oxygen atoms in the chain, which salts better satisfy the set requirements in respect of their color number, yellowing index, periodate number, in particular the UV number after treatment at elevated temperatures, and other characteristics.

We have found that this object is achieved by a process for the preparation of salts of dicarboxylic acids and diamines of the formula I

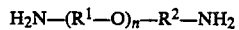

$$H_2N-(R^1-O)_n-R^2-NH_2 \qquad I$$

where $R^1$ and $R^2$ may be identical or different and are each alkylene of 2 to 4 carbon atoms and n is an integer from 1 to 3, which contain hydrazine in the form of hydrazine hydrate.

The use of diamines of the formula I, containing hydrazine in the form of hydrate, for the preparation of salts of dicarboxylic acids has the advantage that the effect of unknown impurities is eliminated in a simple manner, and the characteristics of Such salts, eg. color number, yellowing index, UV number after treatment at elevated temperatures, and periodate numbers and other characteristics, are improved. The diamines used are The diamines used are those of the formula I

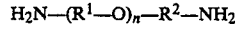

$$H_2N-(R^1-O)_n-R^2-NH_2 \qquad I$$

where $R^1$ and $R^2$ are each identical or different alkylene radicals of 2 to 4 carbon atoms. Examples of suitable radicals are ethylene, 1,2-propylene, 1,3-propylene and 1,4-butylene, ethylene and propylene being preferred. In the diamines of the formula I, n is an integer from 1 to 3, in particular 1 or 2. Examples of suitable diamines are those of the formulae II to VI $$H_2N-(CH_2)_3-O-(CH_2)_2-O-(CH_2)_3-NH_2 \qquad II$$

$$H_2N-CH_2CH_2-O-CH_2-CH_2-NH_2 \qquad III$$

$$H_2N-[CH_2-CH_2-O]_2-CH_2-CH_2-NH_2 \qquad IV$$

$$H_2N-(CH_2)_4-O-(CH_2)_4-NH_2 \qquad V$$

or $$H_2N-(CH_2)_3-O-(CH_2)_4-O(CH_2)_3-NH_2 \qquad VI$$

Diamines of the formula II have become particularly important industrially.

According to the invention, the diamines used contain hydrazine in the form of hydrazine hydrate, the content of hydrazine advantageously being from 5 to 200 ppm, in particular from 10 to 150 ppm.

Examples of suitable dicarboxylic acids are those usually employed for the preparation of nylons. Preferred dicarboxylic acids are alkanedicarboxylic acids of 4 to 12, in particular 4 to 8, carbon atoms. $\alpha,\omega$-Dicarboxylic acids having the stated number of carbon atoms have become particularly important, examples being adipic acid, sebacic acid, azelaic acid and dodecanedioic acid. Examples of other suitable dicarboxylic acids are terephthalic acid and isophthalic acid. The stated dicarboxylic acids may also be used in the form of a mixture. Adipic acid and sebacic acid have become particularly important.

The preparation of salts of dicarboxylic acids and diamines is known per se. As a rule, the diamines and the dicarboxylic acids are reacted in an aqueous solution at elevated temperatures, eg. from 50° to 95° C., so that a 30-65% strength by weight aqueous solution of the salt is obtained. The aqueous solutions thus obtained can be used directly for the preparation of nylons. It is also possible to isolate the particular salts from these solutions by evaporation or precipitation, and to use them for the preparation of nylons.

Nylons obtained from the salts prepared in this manner are useful for the production of filaments, fibers and moldings.

The Examples which follow illustrates the invention.

EXAMPLE

Adipic acid, in the form of a 50% strength by weight aqueous solution, was reacted with an equivalent amount of 4,7-dioxadecane-1,10-diamine at 90° C. The results obtained using different amounts of hydrazine in the form of hydrazine hydrate are shown in the Table below.

TABLE

| | none added | 25 ppm of hydrazine | 50 ppm of hydrazine | 100 ppm of hydrazine |
|---|---|---|---|---|
| Natural color (1) | 7 | 5 | 4 | 2 |
| Yellowing (2) | 156 | 60 | 23 | 16 |
| UV number (3) | 446 | 374 | 273 | 227 |
| Periodate number (4) | 0.111 | 0.055 | 0.021 | 0.007 |
| UV number after 30 minutes at 90° C. | 447 | 469 | 365 | 275 |

(1) Natural color: APHA color number measured at 90° C. on a 40% strength by weight aqueous solution
(2) Yellowing: APHA color number of a 40% strength by weight aqueous solution after heating for 24 hours at 85° C. The extinction was determined using an Elko II photo-

TABLE-continued

| | |
|---|---|
| | meter with S 47 and J 62 filters and a path length of 5 cm. The APHA color number was determined by subtracting extinction (J 62) from extinction (S 47) and using a calibration curve. |
| (3) UV number: | Sum of the extinctions at 226, 282 and 295 um × 100, measured on a 40% strength by weight aqueous solution at 25° C. against doubly distilled water, using a path length of 10 cm. |
| (4) Periodate number: | 1 ml of a 0.5% strength by weight aqueous potassium periodate solution was added to 50 g of a 40% strength by weight aqueous solution of the salt, the mixture was heated for 30 minutes at 90° C. and then cooled to room temperature, and the extinction was measured for a path length of 5 cm, using an Elko II photometer with an S 45 filter. |

We claim:

1. A process for the preparation of a salt of a dicarboxylic acid and a diamine of the formula $$H_2N-(R^1-O)_n-R^2-NH_2 \qquad I,$$

where $R^1$ and $R^2$ may be identical or different and are each alkylene of 2 to 4 carbon atoms and n is an integer from 1 to 3, which comprises: reacting a dicarboxylic acid and a diamine of the formula I which contains hydrazine in the form of hydrazine hydrate, in an aqueous solution at a temperature of from 50° to 95° C.

2. The process of claim 4, wherein a diamine of the formula I contains from 5 to 200 ppm of hydrazine in the form of hydrazine hydrate.

3. The process of claim 4, wherein a diamine of the formula II $$H_2N-(CH_2)_3-O-(CH_2)_2-O-(CH_2)_3-NH_2 \qquad II$$

containing from 10 to 150 ppm of hydrazine in the form of hydrazine hydrate is used.

* * * * *